United States Patent

Bokros et al.

[11] Patent Number: 5,308,361
[45] Date of Patent: May 3, 1994

[54] PROSTHETIC HEART VALVE

[75] Inventors: Jack C. Bokros; Michael R. Emken, both of Austin; Axel D. Haubold, Liberty Hill; T. Scott Peters, Georgetown; Jonathan C. Stupka, Austin, all of Tex.

[73] Assignee: Onx, Inc., Austin, Tex.

[21] Appl. No.: 951,680

[22] Filed: Sep. 25, 1992

Related U.S. Application Data

[63] Continuation-in-part of Ser. No. 674,871, Mar. 25, 1991, Pat. No. 5,152,785, and a continuation-in-part of Ser. No. 837,761, Feb. 18, 1992, Pat. No. 5,192,309, and a continuation-in-part of Ser. No. 888,872, May 26, 1992, Pat. No. 5,236,449.

[51] Int. Cl.$^5$ ............................................. A61F 2/24
[52] U.S. Cl. .................................... 623/2; 137/527
[58] Field of Search ............................ 623/2; 137/527

[56] References Cited

U.S. PATENT DOCUMENTS

| | | | |
|---|---|---|---|
| 4,272,854 | 6/1981 | Bokros | 3/1.5 |
| 4,276,658 | 7/1981 | Hanson et al. | 623/2 |
| 4,328,592 | 5/1982 | Klawitter | 3/1.5 |
| 4,443,894 | 4/1984 | Klawitter | 3/1.5 |
| 4,451,937 | 6/1984 | Klawitter | 137/527 X |
| 4,731,075 | 3/1988 | Gallomezo et al. | 623/2 |
| 5,178,632 | 1/1993 | Hanson et al. | 623/2 |

Primary Examiner—Randall L. Green
Assistant Examiner—Dinh X. Nguyen
Attorney, Agent, or Firm—Fitch, Even, Tabin & Flannery

[57] ABSTRACT

Bi-leaflet heart valves have valve body contours and pivot arrangements that create quick valve response to flow reversal. Valve members or leaflets, which can have flat or curved inflow and outflow surfaces, are slidably and pivotally mounted in a heart valve body of contoured profile so they can be aligned precisely parallel to blood flow in the open position. The leaflets engage either projections extending radially inward from flat wall sections in the valve body sidewall or grooves in these flat wall sections. The shape and relationship of these interengaging surfaces, together with a centrally directed surge of backflowing blood which results from the strategic location of a pair of downstream recesses in the annular valve body, cooperate to provide prompt closing rotation of the leaflets from a parallel open orientation.

11 Claims, 3 Drawing Sheets

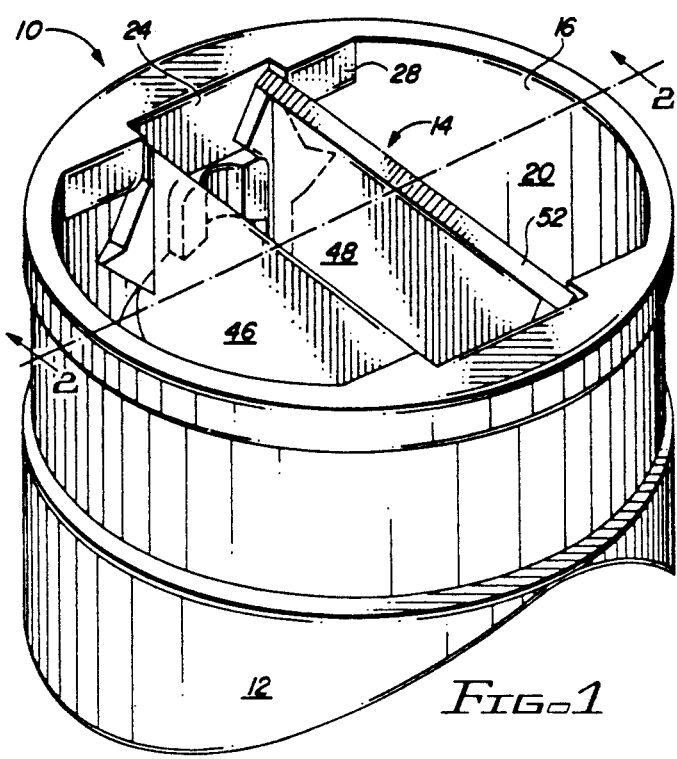
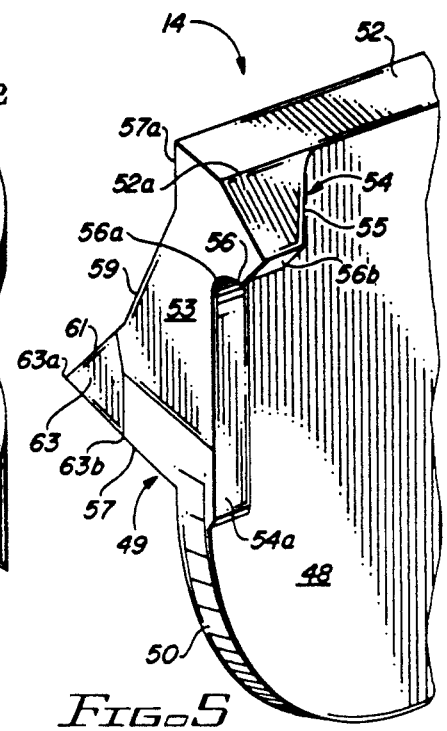
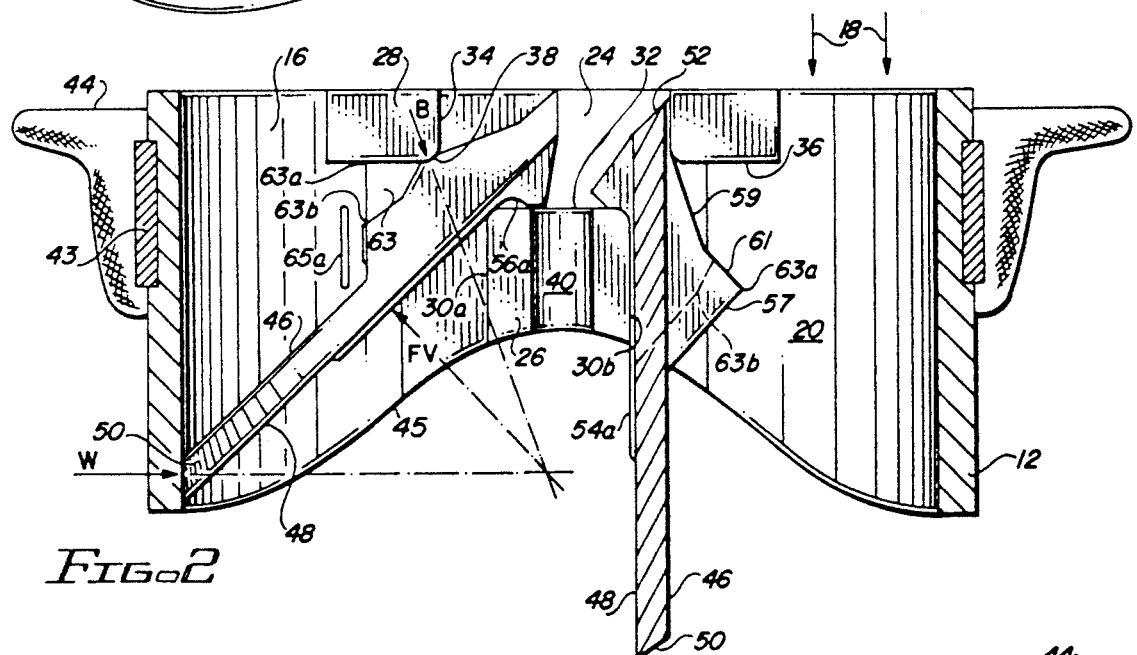
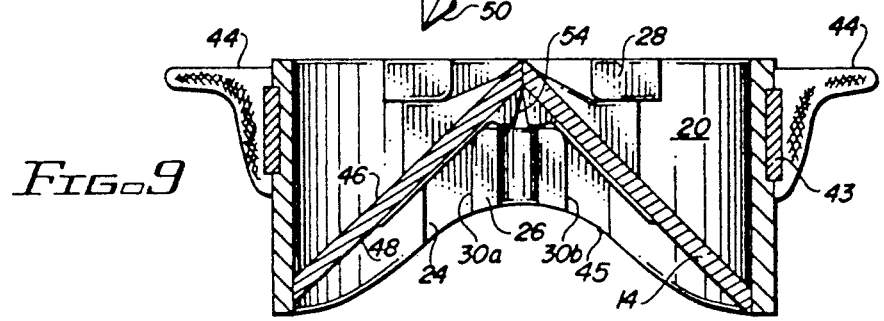

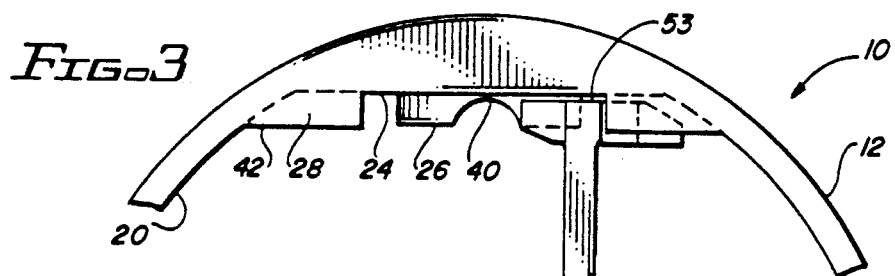
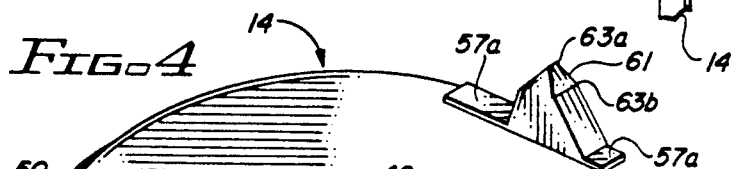
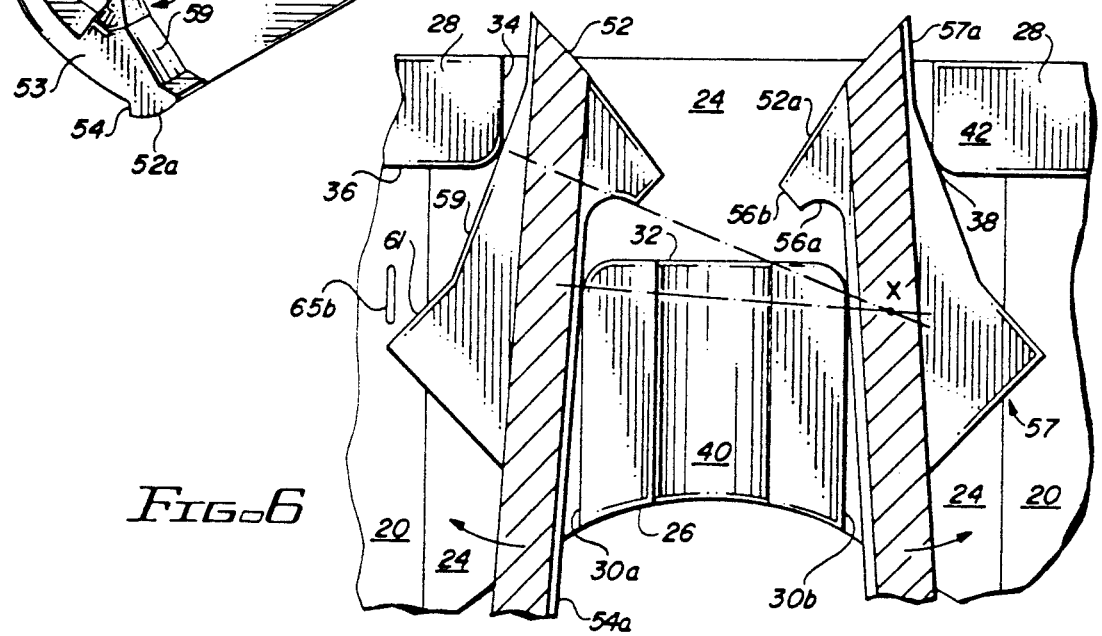
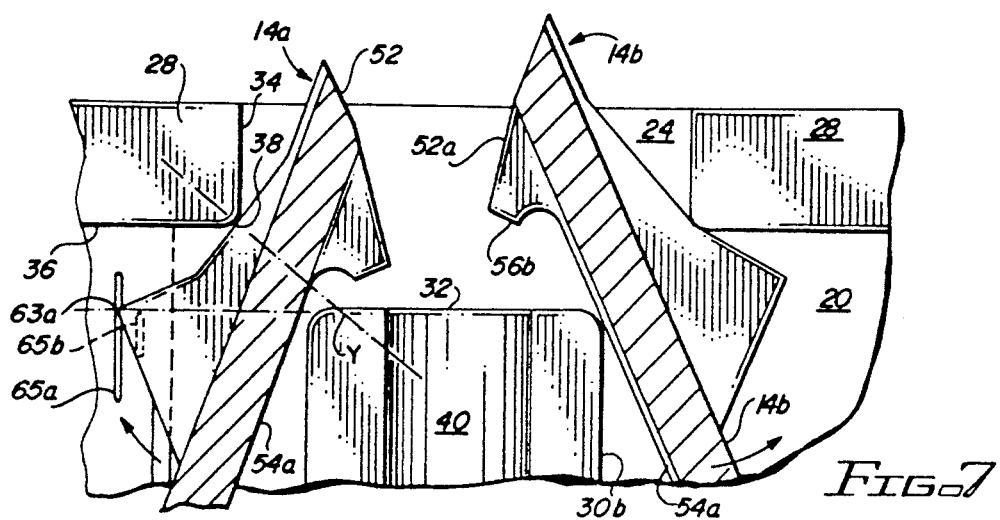

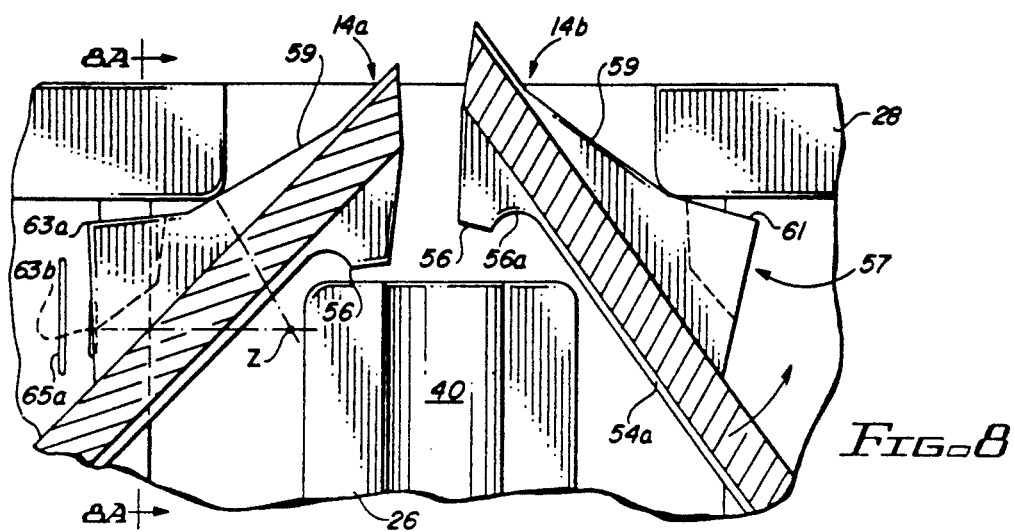
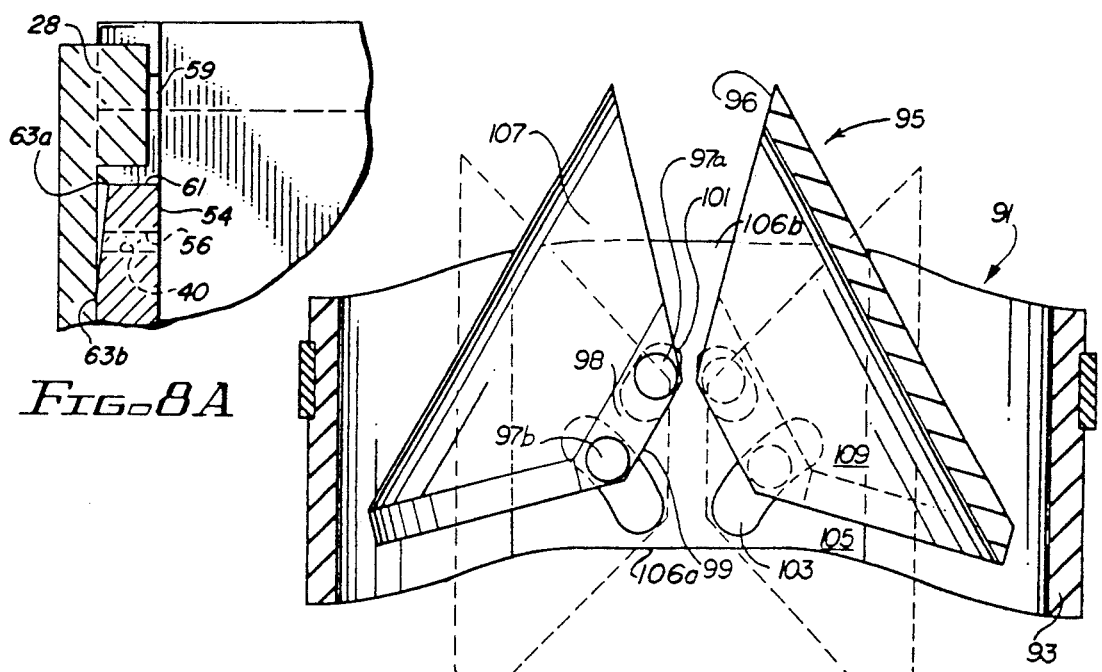
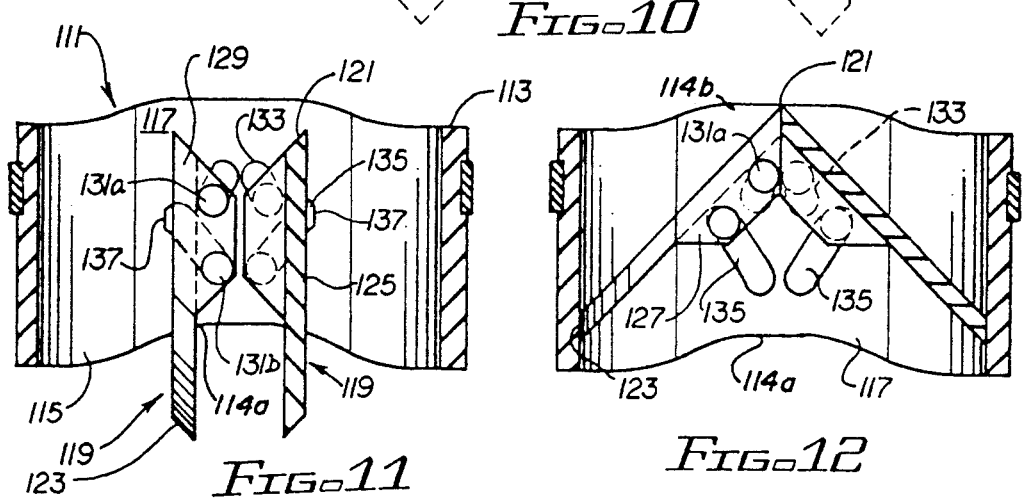

PROSTHETIC HEART VALVE

This application is a continuation-in-part of U.S. application Ser. No. 07/674,871, filed Mar. 25, 1991, now U.S. Pat. No. 5,152,785; Ser. No. 07/837,761, filed Feb. 18, 1992, now U.S. Pat. No. 5,192,309; and Ser. No. 07/888,872, filed May 26, 1992, now U.S. Pat. No. 5,236,449.

BACKGROUND OF THE INVENTION

The present invention pertains to bi-leaflet prosthetic heart valves having two valve members which pivot or both pivot and translate during opening and closing.

DESCRIPTION OF THE PRIOR ART

Various types of heart valve prostheses have been developed which operate hemodynamically as a result of the pumping action of the heart, and a substantial number of bi-leaflet heart valves have been designed. Many of these bi-leaflet valves utilized valve bodies that were substantially cylindrical in profile, having substantially flat inflow and outflow surface boundaries as U.S. Pat. Nos. 4,308,624, 4,692,165 and 4,863,458. There were other valves that modified the profile of the generally tubular valve body to accommodate the location of the pivot mechanism that functionally provided for the movement of the leaflets. For example, U.S. Pat. Nos. 4,272,854 and 4,276,658 included pairs of extensions or standards that were located on the upstream region of the valve body to accommodate sockets which receive ears extending from the opposite lateral edges of the leaflets. In a generally similar fashion, U.S. Pat. Nos. 4,328,592 and 4,443,894 show bi-leaflet heart valves wherein an annular valve body is provided with a pair of standards which extend in a downstream direction from the otherwise generally flat downstream edge, again for the purpose of providing sockets which receive generally hemispherical ears protruding from the lateral edge portions of each leaflet that control the pivoting and translating movement during opening and closing. Examination of these bi-leaflet heart valves shows that the cross section of the interior of each valve body is generally that of an annulus, having a circular exterior surface and a concentric, circular interior surface except for a pair of diametrically opposed flat surfaces; these flat surfaces serve as bearing surfaces against which the flat edges of the leaflets slide during opening and closing and accommodate the mechanisms for guiding the leaflet movement were located.

In general, these mechanical heart valves of the 1970s and 1980s were designed to have relatively low profiles, and the effect of the axial shape or contour of the heart valve body on the flow of blood therethrough was not truly analyzed. In recent years, as the design of mechanical heart valves has become more sophisticated, considerable focus has been placed on providing good flow characteristics so that blood flows through the open valve without adverse boundary layer separation and with a minimum of drag. Moreover, both the entrance flow into such valves, and the exit flow from such valves have been analyzed. It has thus become a more important objective of bi-leaflet heart valve design to provide valves which have superior flow characteristics but which remain particularly responsive to the backflow of blood and cause the leaflets to rapidly move to the closed position and thereby minimize the amount of regurgitation.

SUMMARY OF THE INVENTION

The present invention provides heart valves having the aforementioned desirable characteristics wherein a pair of valve members or leaflets are designed to promptly open and close in response to reversal of the flow of blood, while providing a particularly low-resistance flow path in the open position, thereby resulting in excellent operating characteristics. The foregoing desired characteristics are obtained in certain preferred embodiments where the leaflets can assume an orientation that is parallel to the direction of blood flow in the open position within valve bodies of particular design to promote particularly efficient blood flow therethrough in a downstream direction.

The valves each have a generally annular valve body formed with an interior sidewall, which defines a central passageway therethrough for the passage of blood in a downstream direction, and which has an interior cross section that is circular except for two flat diametrically opposed surfaces against which the flat side edges of the leaflets slide. The valve bodies are provided with a pair of diametrically opposed recesses extending upstream from the downstream edge of the valve body in the regions of the flat interior surface portion, and as a result, these recesses are aligned with a center blood flow passageway region which is located between the pair of leaflets when in the open position. Upon reversal of blood flow, these side openings allow backflowing blood to preferentially enter into this center region and as a result creates a surge of blood in the central passageway region which exerts force against the facing outflow surfaces of the leaflets and results in prompt pivoting of the leaflets to the closed position.

BRIEF DESCRIPTION OF THE DRAWINGS

FIG. 1 is a perspective view of a bi-leaflet heart valve embodying various features of the present invention, shown in its open position;

FIG. 2 is an enlarged cross-sectional view of the heart valve taken along the line 2—2 of FIG. 1, showing the valve with the right hand (RH) leaflet in the open position and with the left hand (LF) leaflet, drawn in elevation, in the closed position;

FIG. 3 is a partial plan view of the bi-leaflet heart valve shown in FIG. 1 with one leaflet removed and one in its open position;

FIG. 4 is a perspective view of a leaflet from the valve shown in FIG. 1;

FIG. 5 is a fragmentary bottom perspective view of the leaflet shown in FIG. 4;

FIG. 6 is an enlarged, fragmentary, cross-sectional view, generally similar to FIG. 2, showing both leaflets shortly after they have begun to move toward the closed position;

FIG. 7 is an enlarged, fragmentary, cross-sectional view, similar to FIG. 6, but this time showing both leaflets in slightly different intermediate positions in their movement toward the closed position;

FIG. 8 is an enlarged, fragmentary, cross-sectional view similar to FIG. 7 again showing both leaflets, in slightly different second intermediate positions in their further movement toward the closed position;

FIG. 8A is a fragmentary sectional view taken along line 8A—8A of FIG. 8;

FIG. 9 is a cross-sectional view of the heart valve of FIG. 1 in the closed position;

FIG. 10 is a cross-sectional view generally similar to FIG. 2 showing an alternative embodiment of a heart valve wherein a pair of curved leaflets are employed and showing the leaflets pivoting toward the closed position from an open position that is shown in broken lines;

FIG. 11 is a cross-sectional view of another alternative embodiment of a heart valve having a pair of leaflets which assume a parallel open position, which valve body has certain features resembling those of the valve shown in FIG. 10; and FIG. 12 is a cross-sectional view of the valve of FIG. 11 with the leaflets shown in the closed position.

DETAILED DESCRIPTION OF THE PREFERRED EMBODIMENTS

FIGS. 1-9 show one preferred embodiment of a heart valve prosthesis 10 constructed according to principles of the present invention. The heart valve has improved flow characteristics when the valve is in a fully open position because boundary layer separation is substantially reduced at major surfaces of the occluders when they are aligned substantially parallel to the valve centerline in the open position, thus minimizing drag. In addition, such heart valves provide a rapid response upon opening and closing, with the contour of the valve body contributing to prompt closing and minimizing regurgitation of blood.

Heart valve 10 includes a generally annular valve body 12 which carries a pair of pivoting occluders or leaflets 14 that open to allow the flow of blood in the downstream direction of arrows 18 (FIG. 2) and close to prevent any substantial backflow. Blood flows through passageway 16 which is defined by a generally cylindrical interior surface or sidewall 20 of valve body 12. The otherwise cylindrical sidewall surface 20 is interrupted by a pair of diametrically opposed, flat wall sections 24. In the general region of each of these flat wall sections are a first centrally located projection 26 and a pair of flanking second projections 28 which coact to define the generally rotative movement of the leaflets 14 when the leaflets move from the fully open position to the closed position, and vice versa.

As evident from FIGS. 1 and 3, these sets of projections 26 and 28, which are positioned at diametrically opposed locations on the valve body, extend generally perpendicularly from the surface of the flat wall sections 24. The central projection 26 has two oppositely facing flat surfaces 30a and 30b, each of which is substantially parallel to the valve centerline, and a second or upstream surface 32 which is preferably transverse, e.g. oriented approximately perpendicular to the valve centerline. The edges between these three surfaces are preferably faceted or rounded (see FIG. 2). In this embodiment, each of the second projections 28 has a flat surface 34 which is oriented substantially parallel to the direction of blood flow, i.e. to the valve centerline, and also has a second, transverse (e.g. generally perpendicular) surface 36; these surfaces intersect at what is termed a downstream edge 38 of the projection 28 (see FIG. 7) which may be faceted or rounded as shown. The middle section 40 of the central projection 26 is preferably concave with respect to the centerline of the valve body 12 so as to minimize the area impeding the flow of blood through the passageway 16. The second projections 28 taper in thickness (see FIG. 3) so as to blend into the sidewall 20 of the valve body at their outer extremities, i.e. having front surfaces 42 which are flat and generally parallel to the flat wall section 24 of the valve body.

The outer surface of the valve body 12 is preferably grooved to receive a metal stiffening ring 43 which in turn supports a sewing ring 44 (see FIGS. 5 and 9). The sewing ring 44 can be of a conventional design as well known in this art. The downstream en,.d of the valve body is contoured to provide a pair of recesses or open notches 45 which extend upward from the downstream edge, where the absence of the valve body sidewall provides such contour and preferably each has the shape of a hyperbola, as best seen in FIGS. 2 and 9. The general function of the recesses 45 in the downstream portion of the valve body is discussed in detail hereinafter along with the operation of the valve.

Referring now to FIG. 2, each leaflet 14 has an upstream-facing or inflow surface 46 and an opposed downstream-facing or outflow surface 48 (with reference to the leaflets when positioned in the closed position). The leaflets can be essentially flat and thus of substantially uniform cross-sectional thickness, except for side sections 49 located along each lateral edge where lugs are formed which coact with the projections 26 and 28 to define the opening and closing movements of the leaflets. Alternatively, the leaflets can have considerably different shapes, such as having a generally cylindrically shaped main body section extending between generally similar pairs of side sections.

Each leaflet 14 has a major arcuate edge surface 50, which is located at the downstream edge of the leaflet in its open position, and a minor mating edge surface 52, which is located at the opposite, upstream edge of the leaflet (again, assuming a leaflet in an open position). The arcuate edge surface 50 preferably has a configuration to abut and seat against the cylindrical sidewall 2 of the valve body in the closed position. The minor edge surface 52 is preferably of a configuration so as to mate with the corresponding mating surface to the opposing leaflet, and this minor surface 52 is oriented at an angle such that the two mating edge surfaces of the leaflets 14 abut while extending across the diameter of the valve passageway when in the closed position, as is well known in the art of bi-leaflet valves. As seen in FIGS. 8 and 9, each side section 49 has a lower beveled section 52a that provides clearance between the two leaflets during their closing and their initial opening movements.

Referring to FIGS. 4 and 5, the leaflets 14 each include a pair of opposed, lateral surfaces 53 which are interposed between the major arcuate surface 50 and the minor mating surface 52. These lateral surfaces 53 of the leaflets are preferably flat, and the leaflets are proportioned so as to provide minimal clearance adjacent the flat wall sections 24 of the valve body 12 (see FIG. 3), so as to enable the leaflets 14 to pivot, with these lateral edge surfaces 53 moving adjacent to the flat wall sections 24, one of which is usually serving as a bearing surface.

Referring to FIG. 5, extending from the outflow surface 48 of each leaflet 14 in each side section 49 is an integral first or opening lug 54. These lugs 54 extend in a direction toward the centerline (in the open position) and have upstream surfaces 52a that are beveled, i.e. slightly angularly offset from the minor edge surface 52; this offset prevents their interference with each other during closing and opening as indicated above. The lugs 54 have downstream surfaces 56 oriented to engage and lie in juxtaposition with the transverse surface 32 of the central projection 26 in the closed position. These surfaces 56 are preferably oriented at an angle of between about 135° and about 150° to the flat outflow surface 48, viz. at an angle of between about 30° and about 45° to the centerline plane in the open position. This downstream surface 56 may be formed with a recess 56a which accommodates the rounded edge of the projection 26, as seen in FIG. 2, when in the open position and prevents the leaflet from escaping downstream. As shown hereinafter, the edge of the downstream projection 26 could be faceted. The radially inward-facing surface 55 of each lug 54 tapered outward toward its base so as to assure the lug has adequate structural strength, as seen in FIG. 5.

Second or closing lugs 57 are also preferably formed in the side sections 49 as an integral part of the leaflets 14 and protrude from the inflow surface 46 of each occluder, with one such lug being located generally along each lateral edge of the leaflet. The second lugs 57 each have a front camming surface 59 which is arranged so as to lie at a desired acute angle to the plane of the flat surface of the major body portion of the occluder, and can have (as best seen in the right hand leaflet of FIGS. 2 and 6) an extension 57a which is oriented parallel to the centerline of the valve body when in the open position. These lugs 57 extend in an upstream direction with the leaflets in the closed position and are sometimes referred to as the upstream lugs. The front camming surfaces are oriented at an angle of between about 5° and about 35°, preferably about 30°, to the centerline plane in the open position. The lug 57 also has a rear angular surface 61 which is oriented at an angle of between about 30° and about 45° to the centerline plane in the open position so as to lie generally in juxtaposition with the transverse surface 36 of the projections 28 when the leaflets are in the closed position. The front camming surface 59 may extend to and meet with the rear surface 61 as shown in the embodiments in FIGS. 1 through 9, or there may be an intermediate surface separating the two or a slight recess at the point of junction.

The radially outer lateral surfaces of the lugs 57 are chamfered near their upper ends to provide a small generally triangular surface 63 on each that generally provides clearance for the lug when it rotates in the region beyond the flat wall 24 of the valve body 12, as best seen in the right hand portion of FIG. 2. The chamfer is precisely located (see left hand leaflet of FIG. 2) so as to create an upper bearing point or ear 63a which engages the curved sidewall of the valve body during an intermediate portion of the closing movement (see FIG. 7) and a lower bearing point or ear 63b which engages the curved sidewall during the later stages of the closing movement of the leaflets. These ears assist in guiding the rotation of the leaflets in the closing movement after the leaflet has lost sliding contact with the downstream projection 26 (which contact is illustrated in FIG. 6); the ears 63a and 63b are best seen in FIG. 5. There are two lines of contact, or rub lines, 65a and b that extend generally parallel to the centerline of the valve body at the locations where there can be contact, respectively, between the upper ears 63a and the lower ears 63b with the valve body sidewall, as best seen perhaps in FIGS. 8 and 8A. The sizing of the leaflets is such that contact of the ears on opposite lateral sides of a leaflet and the respective rub lines will not occur simultaneously. This contact between the lower ear 63b and the curved sidewall 20 of the valve body, which creates the rub line 65b, is shown in the fragmentary cross-sectional view 8A.

In addition to these angular surfaces of the lugs, both lugs include elongated thickening sections 54a and 57a, respectively, that extend parallel to the inflow and outflow surfaces along the leaflet lateral edges 53. These strengthen the lateral regions or side sections 49 of the leaflets where engagement occurs as a result of the pivoting arrangement, while allowing the major body portion of each leaflet 14 to remain relatively thin so it will provide less resistance to blood flow.

The leaflets 14 are installed in the valve body 12 by squeezing the body at diametrically opposed locations, i.e. those where the valve body is cut by the reference line 2—2 in FIG. 1. This causes the diametrically opposed flat wall sections 24 to further separate, thus allowing the leaflets 14 to be fitted into the passageway 16 of the valve body. The side sections 49 at the lateral edge regions of the leaflets containing the first lugs 54 and second lugs 57 are received between the projections 26 and the projections 28 of the valve body. When the squeezing force is removed, the valve body 12 returns to its original configuration, leaving the desired minimal clearance between the flat wall sections 24 of the valve body 12 and the lateral edge surfaces 53 of the leaflets as discussed above. The locations of the projections 26 and the projections 28 is such that the leaflets may initially translate slightly but then quickly begin to rotate in traveling from the open to the closed position, while the leaflets always are maintained in functional operating attitudes. This is discussed further below in relation to the operation of the valve.

The leaflets are slidably-pivotally mounted for travel between closed and open positions, and the leaflets 14 are oriented parallel to the valve centerline in the open position to create minimal turbulence and flow separation. The illustrated design incorporating the valve body downstream contour allows such a precisely parallel orientation to be achieved while assuring that the leaflets close very rapidly as soon as flow reversal occurs.

For illustration and comparison purposes, FIG. 2 shows the valve 1? with the left-hand leaflet in the closed position and with the right hand leaflet in the full open position, although it should be understood that such an orientation would never occur as the two leaflets 14 move substantially simultaneously with each other. In this respect, attention is directed to FIGS. 6 and 9 of the drawings wherein representative movement of the pair of leaflets from the open to the closed position is illustrated. FIGS. 7 and 8 show intermediate position with the RH and LH leaflets having different orientations for purposes of explanation.

The fully open leaflet position is shown on the right hand side of FIG. 2 wherein the recess 56a of the first lug 54 is in contact with the rounded edge between the surfaces 30 and 32 of the first or central projection 26. The flat extension portions 54a of the first lugs (along the outflow surfaces) are in contact with the surface 30b of the projections 26 and thus lie substantially parallel to the centerline. The thin parallel extensions 57a of the lug 57 are similarly in contact with and lie in juxtaposition to the surface 34 of the projection 28 (which surface is also parallel to the centerline). Thus, in the open position, the major body portion of each leaflet extends substantially parallel to the valve centerline, thus providing minimum obstruction to the downstream flow of blood and defining a central passageway region between the outflow surfaces 48 of the pair of flat leaflets and two side passageway regions, which are defined by the inflow surfaces 46 of the leaflets and the cylindrical interior surface or sidewall of the valve body.

Upon the reversal of blood flow as a result of the contraction of the heart, the backflow of blood creates a drag on the surfaces of the leaflet, displacing it upwardly (with reference to FIGS. 2 and 6). A very brief initial movement may be one of pure translation, i.e. all points on the body are simultaneously moving in the same direction at the same velocity, with the amount of translation being dependent upon the location of the upstream end of the camming surface 59 and the amount of tolerance in the spacing between projections 26 and 28. The presence of the front camming surface 59 causes the leaflet 14 to substantially immediately begin to rotate (see FIG. 6) as it continues to slide upward, maintaining contact between the camming surfaces 59 and the curved edges 38 of the upstream projections 28. During the first phase of closing movement, contact is likely maintained between the extension regions 54a of the first lug and the curved upstream edges of the center projection 26; however, this contact depends upon the spacing (in the generally radial direction) between the central projections 26 and the flanking projections 28 and upon the dynamic conditions within the bloodstream.

As soon as backflow begins, because of the presence of the side openings provided by recesses 45, there will be an initial surge of blood flow in the central passageway between the facing leaflets because blood can enter the valve from the surrounding chamber not only axially, as is substantially the case with regard to the two side passageways, but also laterally through the side openings provided by the recesses in the regions downstream of the flat sidewalls. This preferential directing of the initial surge of backflowing blood through the central passageway region between the outflow surfaces 48 of the leaflets, in addition to exerting the drag forces mentioned above, exerts forces perpendicular to the surfaces of the eccentrically mounted leaflets, and these forces substantially assist in causing the desired closing rotation to promptly occur. Rotation continues to expose the outflow surfaces 48 of the leaflets to more and more of the full force of the backflowing stream of blood, thereby amplifying the rotative force vector being applied against each leaflet. Moreover, the backflow of blood which enters through the region of the recesses continues to act effectively until closing is complete. The hyperbolic shape of the recesses 45, which preferably extend upstream a distance of at least about 33 percent of the axial length or height of the valve body, and preferably about 40 percent (as shown in FIG. 2) or more, is considered particularly effective for channeling the backflowing blood to the central passageway while still retaining overall good flow characteristics through the valve.

Illustrated in FIG. 7 are leaflet positions where continued sliding-pivotal movement has occurred. As illustrated, contact of the left hand leaflet 14a with the downstream projection 26 has ended so that further movement is being defined by the camming surface 59 and the upper ears 63a, which have moved into engagement with the curved sidewall 20 along the rub line 65a, the upper end of which is shown as being approached. Once the end is reached, the next movement of the leaflet will be defined by the camming surfaces 59 and the lower ears 63b which will travel upward along the shorter rub lines 65b (which as shown in FIGS. 6 and 7 are located slightly nearer the valve centerline when projected onto a plane perpendicular to the pivot axis of the leaflet). When the lower ears 63b have nearly reached the upper ends of the rub lines 65b, the travel of the camming surface 59 along the downstream projection edge 38 is such that the junction between the front and rear surfaces 59, 61 has nearly been reached (as illustrated generally in FIG. 8 with respect to the left hand leaflet).

Depending upon external forces upon the patient and/or dynamic forces within the bloodstream at the valve, the intermediate position illustrated by the right hand leaflet in FIG. 7 may be reached, where the sliding-pivoting movement has been such that the junction between the front camming surface 59 and the rear surface 61 has reached the downstream edge 38 of the projection 28 without any contact of either of the ears 63a,b with the rub lines 65a,b. Thereafter final movement is generally one of rotation about a fixed pivot point. As shown in FIG. 8, as this pure rotation of the right hand leaflet 14b continues, the primary function of the upstream projection 28 is one of pivotal support for the leaflet at the junction between front camming surface 59 and the rear surface 61, and contact between the lug extensions 54a and the central projections 26 has terminated at this stage of the movement.

It is anticipated that leaflet movement will generally follow the path of the left hand leaflets 14a in FIGS. 7 and 8, with the locations of the ears 63a and 63b playing a part in defining the precise CRP (center of rotation of pivot) for each leaflet as the closing movement continues. The CRP is located by drawing perpendiculars to the leaflet surface at each point of contact to see where they intersect. The left hand leaflet 14a in FIG. 8 should continue to travel so that the lower ear 63b reaches the top of the rub line 65b at the same time as the downstream end of the camming surface 59 reaches the edge 38 of the projection 28. However, depending upon the extent of the chamfer which creates the triangular surface 63, contact between the ear 63a and the sidewall might cease as the leaflets are in their final approach to the fully closed position, which is still acceptable.

The last phase of the movement occurs when the arcuate downstream edge 50 (see FIG. 2) of the leaflet makes contact with the interior sidewall of the valve body. Whichever leaflet happens to close first, i.e. its major arcuate edge is the first to contact the sidewall 20, the mating edge surface 52 of that leaflet may extend past the centerline by 1 or 2 thousandths of an inch, if it is slightly oversized but within manufacturing tolerance; however, such a situation will be accommodated when the second of the two leaflets reaches the fully closed position, thereby positively assuring that there is contact between the primary flat facing surfaces of the mating edges 52.

FIG. 9 shows the leaflets in their closed position which illustrates another advantageous feature of the valve body design, namely effective operation with each leaflet only rotating an angular amount from its parallel orientation in the open position of between about 30° and about 50°. Whereas previously it was felt that flat leaflets should generally form angles of about 65° with the valve centerline in the closed position (see U.S. Pat. Nos. 4,692,165 and 4,863,458 for example) to minimize the height of the valve body, with the present construction, the leaflets are preferably oriented with their flat main body surfaces 46, 48 at a downstream angle of between about 40° and about 50° to the centerline plane in the closed position. In the illustrated position, the surfaces 46 form an angle of about 50° with centerline plane, which means that they only had to rotate this angular amount, i.e. about 50°, to reach the closed position, and the smaller the amount of rotation, the smaller the amount of regurgitation of blood.

As soon as the next cycle occurs so that there is again a flow of blood in the normal downstream direction through the valve, the force of the blood on the inflow surfaces 46 of the leaflets 14 causes their immediate displacement slightly downward until the surface 56b of the first or opening lug 54 contacts the upstream-facing surface 32 of the center projection 26. This causes pivoting of the leaflets in the opening direction to occur, with such pivoting being primarily guided by the engagement between the surfaces 56 and 54a of the opening lugs 54 with the center projection 26 between the ears 63a and 63b and the valve body sidewall. Such rotation continues until the fully open position is reached with the leaflets 14 in a substantially parallel position with respect to the valve centerline. In this position, the rounded upstream edges of the projection 26 interengage with the recesses 56a, and the downstream-facing surfaces 56 of the lugs 54 engage the transverse surface 32. The projection side surfaces 30 are also in juxtaposition with the flat surfaces of the thin lug extensions 54a, and the shorter extensions 57a of the upstream lugs 57 lie in juxtaposition with the side surfaces 34 of the upstream projections 28, thus assuring stable support in this open orientation until the next reversal of blood flow.

A particularly advantageous pivot arrangement is created by the use of projections 26, 28 spaced apart in this manner (which extend from the two diametrically opposed flat sidewall sections 24 of the valve body) in conjunction with the oppositely extending lugs 54, 57 located along the lateral edges of each leaflet. There is a prompt and rapid rotation of the leaflets 14 about a center of rotation of pivot (CRP) that initially is spaced a significant distance, preferably at least a distance equal to one-half the radius of the valve passageway, beyond the outflow surface of the leaflet when closing movement first begins. For example, in FIG. 6, which illustrates the position after a slight amount of rotation has actually taken place, the CRP for the left hand leaflet is at point X a substantial distance on the opposite side of the centerline plane of the valve, i.e. the plane which contains the centerline of the passageway and is parallel to the axes of rotation of the valve members, most preferably this distance is equal to at least half the radius of the passageway. As a result, there is a very large initial effective torque which, along with the direction of the initial surge of backflowing blood into the central passageway guided by the hyperbolic recesses 45, drives each leaflet in its rotational movement; this assures a prompt response in getting the leaflets moving toward the closed position which minimizes regurgitation of blood. There is also a similar, large moment arm which contributes to achieving prompt initial rotational movement of the leaflets moving to the open position.

The term CRP is used to describe the theoretical instantaneous pivot center about which rotation of the leaflet is occurring at any instant in its movement from the open position to the closed position. Where there is contact at two locations along each lateral edge region of the leaflet, i.e., with the projection 28 and with either the projection 26 or the valve body sidewall at one of the rub lines 65, the CRP is determined by constructing perpendiculars to the respective surfaces of the leaflet at the precise points where contact occurs and then determining the point where those perpendiculars cross. The CRP is shown for the left hand leaflet in FIG. 6 as point X, in FIG. 7 as point Y and in FIG. 8 as point Z, with the latter two points being close to the outflow surface 48. On the other hand, when the leaflets shift to the locations shown for the right hand leaflets 14b in FIGS. 7 and 8, the CRP is thereafter located at the junction between the camming surface 59 and the near surface 61, which is slightly beyond the inflow surface 46.

Comparison will show that there is initially a very large rotational moment arm because the CRP was initially spaced a relatively long distance from the point on the outflow surface of the leaflet which corresponds to the point at which a single vector can be applied that will be equivalent to the sum of all of the closing (or opening) forces upon the leaflet. Such a point can be computed to be generally located close to the geographic center of the outflow surface 48 in the late stages of closing, but in the early stage of lift upon a flat plate such as this, the composite force vector (FV) is computed to act through a central point located about 25% of the length of the leaflet from the edge 50 which is the leading edge with respect to the backflow of blood. It should be apparent that this moment arm, defined by the distance between this point and the CRP, has been considerably shortened in FIGS. 7 and 8. Moreover, in FIG. 8, the CRP for the right hand leaflet 14b is at or very near the intersection between the front camming surface 59 and the rear surface 61 of the closing lug 57. The result of the shortening of the distance between the CRP and the point at which the composite force vector is being applied, as a result of migration of the CRP from a point far beyond the outflow surface (in the direction away from the occluder) to a point near the surface of the leaflet, is particularly advantageous. It results in a reduction in the closing impact of the leaflet and also in a reduction of the amount of any final sliding movement of the leaflet in reaching the closed position at a time when the pressure differential across the leaflet is highest and thus would contribute the greatest to wear.

As shown in FIG. 2 with respect to the left hand leaflet in FIG. 2, at the point of closure, the closing force is represented by the composite closing force vector FV, and the opposite and equal forces are the force W (at which the arcuate edge 50 of the leaflet bears against the cylindrical sidewall of the valve body) and the force vector B, which is located at the point of engagement between the camming surface 59 and the downstream edge of the projection 28. In the illustrated embodiment, the orientation of the camming surface 59 is such that the force vector B is applied along a line so that these three forces meet at about a point Q so there is no final closing torque, reducing wear.

Illustrated in FIG. 10 is an alternative embodiment of a heart valve 91 which has a valve body 93 which is contoured along both its upstream edge and its downstream edge to provide an elongated valve body of substantially uniform axial length about the entire 360° periphery. The valve 91 employs a pair of leaflets 95 which are generally sections of a tube of elliptical cross section and which have mating upstream edges 96. Each leaflet 95 has a pair of ears of circular cross section; these ears can be generally frustoconical in shape and protrude from lateral flat surface sections 98 located along lateral edge surfaces 99 of each leaflet. The details of the construction are described in U.S. Pat. application Ser. No. 888,872 now U.S. Pat. No. 5,236,449, filed May 26, 1992, the disclosure of which is incorporated herein by reference.

Two pairs of slots 101, 103 are provided in each of two diametrically opposed flat sidewall sections 105 of the valve body 93. The slots 101 which lie upstream in each pair are straight and slightly angled with respect to the centerline plane through the valve body, i.e. the plane which is perpendicular to the flat sidewall 105 and contains the axial centerline of the valve passageway. The downstream slots 103 are arcuate, being concave in a generally downstream direction and being constructed to have sidewalls of generally similar curvature which are aligned with each other about a common center. The valve body 93 is provided with a pair of downstream recesses 106a and with a pair of upstream standards or extensions 106b having complementary shape to that of the recesses.

In FIG. 10, the leaflets 95 are shown in the open position in phantom outline, in which orientation, the convex inflow surfaces 107 and the concave outflow surfaces 109 are all aligned parallel to the centerline through the valve passageway. When the backflow of blood occurs following the end of each pumping stroke, the drag of the blood on the surfaces of the leaflets 95 causes them to translate upstream. The upstream ears 97a of the pair move upward in the slightly angled slots 101 and therefore move slightly closer to the centerline plane. The downstream ears 97b slide upward in contact with the upstream concave arcuate edge of the downstream slots 103 and cause the right-hand leaflet 95 to immediately begin to pivot in a counterclockwise direction about an axis defined by the coaxial upstream cylindrical ears 97a. The recesses 106a direct a surge of backflowing blood into the central passageway (between the pair of curved leaflets as depicted in the broken line outline in FIG. 10) and again aid in providing forces against the outflow concave surfaces of the leaflets that assure prompt initial closing movement. The pivot axis of course is continuously changing as the ears 97a slide upstream toward the upstream ends of the slots 101. FIG. 10 depicts the leaflets in an intermediate closing position (with the left hand leaflet shown in elevation) where there is contact between the ears 97a and the upstream sidewalls of the slots 101 and also contact between the ears 97b and the concave upstream sidewalls of the slots 103. Following complete closing of the leaflets 95, opening movement of the leaflets 95 occurs on the next pumping stroke of the heart with the ears 97a, 97b sliding downward in the slots 101, 103 in contact with the downstream edges thereof.

Depicted in FIGS. 11 and 12 is a valve 111 generally similar to that shown in FIG. 10 which utilizes a pair of leaflets 119 in the form of flat plates. The heart valve 111 has a valve body 113 that is contoured or scalloped along both its upstream and downstream edges to provide a pair of generally hyperbolic downstream recesses 114a and a pair of upstream extensions 114b of complementary shape. Therefore, similar to the valve body of the heart valve 91, the valve body 113 has a substantially uniform axial length about its entire 360° periphery. It has a generally cylindrical interior wall 115 that is interrupted at diametrically opposite locations to provide a pair of flat interior wall sections 117 wherein slot patterns are provided for mounting a pair of leaflets 119. Again, for purposes of illustration, the left-hand leaflet is shown in elevation whereas the right-hand leaflet is shown in section as in the case of the heart valves shown in FIGS. 2 and 10. Each of the leaflets has a flat upstream mating edge 121 and an arcuate downstream edge 123. The leaflets have main body portions 125 in the form of flat plate portions of uniform thickness and have side extensions 127 having a thickness about twice that of the main body portions. The lateral surfaces of the side extensions are flat surfaces 129 from which a pair of ears 131a and 131b protrude. The ears 131 are received in pairs of slots 133, 135 provided in the flat interior wall sections 117 of the valve body.

In the open position illustrated in FIG. 11, the flat main body portions 125 of the leaflets are oriented parallel to the centerline through the valve, and thus the major inflow and outflow surfaces of each of the leaflets 119 is precisely parallel to the centerline plane, i.e. the plane which contains the centerline of the valve passageway and is perpendicular to the pair of diametrically opposed flat sidewall portions 117. This arrangement creates a central passageway region and two side passageway regions which are approximately equal in cross sectional area so there is very substantial blood flow adjacent both the outflow and inflow surfaces of each leaflet. In the open position, the ears 131a and 131b are located at the downstream ends of the respective slots 133, 135. As the backflow of blood begins at the end of a pumping stroke, the drag of the upstream flowing blood on the inflow and outflow surfaces of the leaflets 119 causes the leaflets to be displaced in an upstream direction. The ears 131 move upward in the slots 133, 135, again causing pivoting of the leaflets to occur about the coaxial upstream ears 131a which are themselves sliding upward against the upstream sidewalls of the slots 133. The upstream slots are oriented at a downstream angle of about 35°, and thus the ears 131a move closer to the centerline plane as the closing pivoting movement continues. The downstream slots 135 are oriented at an upstream angle of about 45° to the centerline plane and are longer in length than the upstream slots 133, resulting in a combined pivoting or rotational movement of the leaflets toward the closed position orientation depicted in FIG. 12. The downstream recesses 114a, as best seen in FIG. 11, create a surge of backflowing blood into the central passageway region between the facing outflow surfaces of the leaflets 119; this surge, as described in respect of the heart valve 10 of FIGS. 1 through 9, assures prompt rotation of the leaflets toward the closed position orientation as a result of exerting increased forces against the surface regions of the facing outflow surfaces of the leaflets.

In FIG. 12, where the completely closed position is illustrated, the mating surfaces 121, which are located at the upstream edges of each of the two leaflets 119, are in contact with each other. The side extensions 127 of the leaflets have their upstream ends contoured so as to be extensions of the mating edges 121, and thus they can also abut each other. At the same time, the downstream arcuate edges 123 of the leaflets are seated against the cylindrical sections 115 of the interior wall of the valve body, thus providing a good seal at these locations. Preferably, the upstream end wall of each slot 135 is provided with an oblique short flat surface 137 which creates an overall force vector that assures tight closing at the upstream mating edges 121. In the closed position, the ears 131a will be at or closely adjacent the upstream ends of the slots 133. When normal downstream blood flow resumes at the beginning of the next pumping stroke, the ears 131 translate downstream in the slots 133, 135, sliding in engagement generally along the downstream sidewalls until they reach the bottom thereof and causing pivoting of the leaflets to the open position shown in FIG. 11.

When the valve is open, the overall uniform axial length of the heart valve body proves to be an advantage in conjunction with the three flow passageway regions of substantially equal cross-sectional area. Because all three passageway regions are equal in cross-sectional area and also equal in axial length, potential flow imbalances between regions are eliminated. As a result, the undesirable likelihood of having a valve develop an imbalanced, high, central jet of blood flow through the central passageway region is positively avoided. Moreover, it has been found that a valve body of longer axial length produces less turbulent flow through its passageway regions and results in a lower pressure drop.

Although the invention has been described with respect to a number of preferred embodiments, which include the best mode believed to achieve these objectives in prosthetic heart valves, it should be understood that various changes and modifications as would be obvious to one having the ordinary skill in this art may be made without departing from the scope of the invention which is defined by the claims appended hereto. Particular features of these heart valves are emphasized in the claims which follow.

What is claimed is:

1. A bi-leaflet prosthetic heart valve comprising
an annular valve body having an upstream end, a downstream end and a central passageway therethrough for blood flow, which passageway has an axial centerline,
two leaflets mounted in valve body, each having an inflow surface and an outflow surface,
pivot means formed on said leaflets and said valve body which define paths of movement of said leaflets on eccentric pivot axes between an open position which allows blood flow through said central passageway and a closed position which blocks blood flow therethrough, said paths of movement being such that downstream edges of said leaflets move outward away from the axial centerline to reach the closed position in which said outflow surfaces face generally downstream,
said valve body having a generally cylindrical interior sidewall of generally circular cross section which is interrupted with a pair of diametrically opposed flat sidewall sections wherein portions of said pivot means are located,
said valve body being contoured in an axial direction with a pair of open notches extending laterally through said sidewall in the downstream end laterally through said sidewall in the downstream end thereof located in generally axial alignment with said flat sidewall sections, which notches provide a pair of side openings that extend a substantial distance upstream from farthest downstream points along said valve body's downstream edge, which side openings are laterally aligned with a central passageway region located between said two leaflets in the open position so that, upon reversal of blood flow, backflowing blood laterally enters said valve body passageway through said side openings and results in a surge of blood flow into said central passageway region between said two leaflets, the forces which are exerted by such blood flow in said central passageway region against said leaflet outflow surfaces causing prompt pivoting of said eccentrically mounted leaflets toward their closed position orientation.

2. A heart valve according to claim 1 wherein said leaflets can assume an orientation aligned substantially parallel to said axial centerline in said open position.

3. A heart valve according to claim 2 wherein said pivot means includes first interengaging means on said leaflets and second interengaging means on said valve body and wherein said pivot means is constructed so that said first interengaging means on said leaflets translate upstream relative to said second interengaging means and pivot as part of said movement from the open position to the closed position.

4. A heart valve according to claim 1 wherein said leaflets have generally flat main body sections which are substantially parallel to each other.

5. A heart valve according to claim 1 wherein said open notches are generally hyperbolic in shape.

6. A bi-leaflet prosthetic heart valve comprising:
an annular valve body having an upstream end, a downstream end and a central passageway therethrough for blood flow, which passageway has an axial centerline,
two leaflets mounted in said valve body, each having an inflow surface and an outflow surface,
pivot means formed on said leaflets and said valve body which define paths of movement of said leaflets on eccentric pivot axes between an open position which allows blood flow through said central passageway and a closed position which blocks blood flow therethrough, said paths of movement being such that downstream edges of said leaflets move outward away from said axial centerline to reach the closed position in which said outflow surfaces face generally downstream,
said valve body having a generally cylindrical interior sidewall of generally circular cross section which is interrupted with a pair of diametrically opposed flat sidewall sections wherein said pivot means are located,
said valve body being contoured in an axial direction along both axial ends, with a pair of diametrically opposed upstream extensions which are aligned with said flat wall sections and which extensions extend a substantial distance upstream beyond said valve body's remaining upstream periphery, and with a pair of open notches in said valve body's downstream end located in generally axial alignment with said flat sidewall sections, which open notches extend laterally through said sidewall to provide a pair of side openings that extend a substantial distance upstream from said valve body's remaining downstream edge, said side openings being laterally aligned with a central passageway region located between said two leaflets in the open position so that, upon reversal of blood flow, backflowing blood laterally enters said valve body passageway through said side openings and results in a surge of blood flow into said central passageway region between said two leaflets, the forces exerted by such blood flow in said central passageway region impinging upon said leaflet outflow surfaces and resulting in prompt pivoting of said eccentrically mounted leaflets toward their closed position orientations.

7. A heart valve according to claim 6 wherein said valve body has an axial length which is substantially constant about the periphery thereof.

8. A heart valve according to claim 7 wherein said leaflets have generally flat main body sections which are substantially parallel to each other.

9. A heart valve according to claim 7 wherein said leaflets are mounted so that when they are in the open position they create three flow passageway regions through the valve of substantially equal cross-sectional area.

10. A bi-leaflet prosthetic heart valve comprising an annular valve body having an upstream end, a downstream end and a central passageway therethrough for blood flow, which passageway has an axial centerline, two leaflets mounted in valve body, each having an inflow surface and an outflow surface, and pivot means formed on said leaflets and said valve body which define paths of movement of said leaflets on eccentric pivot axes between an open position which allows blood flow through said central passageway and a closed position which blocks blood flow therethrough, said paths of movement being such that downstream edges of said leaflets move outward away from said axial centerline to reach the closed position in which said outflow surfaces face generally downstream, said valve body having a generally cylindrical interior sidewall of generally circular cross section which is interrupted with a pair of diametrically opposed flat sidewall sections wherein said pivot means are located, and said valve body being contoured in an axial direction along both axial ends, having a pair of diametrically opposed upstream extensions which are aligned with said flat wall sections and which extensions extend a substantial distance upstream beyond said valve body's remaining upstream periphery, and having said valve body's downstream end similarly contoured in axial alignment with said upstream extensions to provide a pair of side openings and create a valve body having an axial length which is substantially constant about the periphery thereof, said side openings being laterally aligned with a central passageway region located between said two leaflets in the open position so that, upon reversal of blood flow, backflowing blood laterally enters said valve body passageway through said side openings and results in a surge of blood flow into said central passageway region between said two leaflets, the forces exerted by such blood flow in said central passageway region impinging upon said leaflet outflow surfaces and resulting in prompt pivoting of said eccentrically mounted leaflets toward their closed position orientations.

11. A heart valve according to claim 10 wherein said leaflets are mounted so that when they are in the open position they create three flow passageway regions through the valve of substantially equal cross-sectional areas.

* * * * *